United States Patent [19]

Weilbach et al.

[11] 4,310,224
[45] Jan. 12, 1982

[54] PRECISELY MOVABLE MIRROR MOUNT

[75] Inventors: August Weilbach, LaHabra; Charles W. Ragsdale, Concord; Corles M. Perkins, Santa Ana, all of Calif.

[73] Assignee: Cavitron Corporation, New York, N.Y.

[21] Appl. No.: 88,199

[22] Filed: Oct. 23, 1979

[51] Int. Cl.³ .......................... A61B 3/02; F16C 1/10
[52] U.S. Cl. .................................. 351/23; 74/501 M
[58] Field of Search ................. 351/23, 24; 74/501 M

[56] References Cited

U.S. PATENT DOCUMENTS 4,045,130  8/1977  Krahn .................................. 351/24

OTHER PUBLICATIONS

Coherent, The New Standard of Excellence in Visual Field Training, Perimetron Computerized Projection Perimeter, Sep. 1976.
Coherent, The Use of Computers to Automate Visual Field Exams is Resulting in Quicker More Complete Data Independent of Operator Skill, Perimetron, Aug. 1978.

*Primary Examiner*—John K. Corbin
*Assistant Examiner*—Rodney B. Bovernick

[57] ABSTRACT

A precisely movable mirror mount has a mirror pivotally supported on an elongated member. The member is rotationally supported by a support spaced along the member from the mirror, the support also supporting a winch. One end of a strand is windingly connected to the winch and the other end of the strand is connected to the mirror for rotating the mirror in one direction against a bias device which urges mirror rotation in the other direction. The strand mirror-rotating arrangement makes the device slim and thus visually non-distracting and the spacing to the member and winch support minimizes noise at the mirror to make the device audibly non-distracting, both of which are important to the preferred use of the device in a visual field tester in which the patient is close to the device.

10 Claims, 2 Drawing Figures

PRECISELY MOVABLE MIRROR MOUNT

BACKGROUND OF THE INVENTION

The invention relates to a precisely movable mirror mount and, more particularly, to a mirror mount for use in a visual field tester.

Some people have impaired visual fields. These people cannot see at all or as well at certain solid angles from the visual axis of at least one of their eyes as can people with normal vision. This condition can, for example, arise from a damaged or imperfectly formed retina.

It is sometimes desirable to be able to determine the shape and extent of such visual field impairment for, for example, ascertaining changes in the condition through successive examinations to assess a treatment for the condition. Devices for testing visual field impairments are therefore available.

One type of visual field tester which is often referred to as a Goldman-type tester has a screen on which a light spot is projected in various positions relative to the visual axis of the eye being examined. The patient's ability to see the spot in the various positions relative to his visual axis which is fixed by looking at a fixation target, and the relative intensity of the light spot which can be seen can then be plotted to indicate the shape and extent of the patient's visual field impairment. In the Goldman-type device, a pantograph-like, mechanical arm arrangement links a device for projecting the light spot onto the screen to a handle for controlling the aim of the spot projection. The projector is positioned in front of the patient so as to be able to project the light spot to all portions of the screen, although sufficiently adjacent the patient as not to block the patient's view of the screen, and the pantograph-like arm arrangement extends to the other side of the screen so that the operator can observe the patient to check the patient's fixation of the optical axis of the eye being examined on the fixation target. This arrangement, although convenient for operation, places the entire pantograph-like arm arrangement adjacent and in front of the patient to distract the patient's necessary fixation of the optical axis with the sound or sight of the movement for positioning the light spot from the projector.

The Goldman-type tester also has a pen recorder associated with the handle end of the pantograph-like arms for recording the spot positions the patient can or cannot see. The light spot is progressed along a radial meridian toward or away from the fixated visual axis until, for example, the patient cannot see it. This procedure is repeated along sufficient meridians to define successive points at the ends of the meridian lines recorded by the pen at which the patient has equal visual limits. These points can then be connected graphically by a line called an isopter which displays the field of the patient's vision under the test conditions. The pen recording from the test device must, therefore, be further processed graphically to achieve the desired isopter plot.

The manual operation of the pantograph-like arms, the constructional complexity of the arm arrangement, the patient distraction in sound or sight from fixing the visual axis at the fixation target from the movement of the mechanical arms adjacent the patient for variably positioning the testing light spot, and the need to further manually process the pen recording of the patient's visual ability to develop the desired isopters all tend to limit the desirability of Goldman-type visual field testers. A way of precisely and automatically projecting a light beam which is visually and audibly less distracting and which, from the automatic positioning control, could also automatically develop isopters would thus be desirable.

SUMMARY OF THE INVENTION

It is therefore an object of the invention to provide a precisely movable mirror mount which may be used, for example, to positionably project a light beam.

It is a further object of the invention to provide an improved light projector for a visual field tester.

To these ends, the invention has an elongated member on which a mirror is pivotally supported for rotation about an axis generally normal to the longitudinal axis of the member. A support supports the member at a point spaced from the mirror for rotation about the longitudinal axis of the member, and also supports a winch. One end of a strand is windingly connected to the winch and the other end is connected to the mirror at a distance from the rotation axis of the mirror. Rotation of the winch to wind up the strand will thus rotate the mirror in one direction. A bias device such as a spring is connected between the member and mirror to urge rotation of the mirror in the other direction.

Rotation of the member about its longitudinal axis will thus control the azimuth of the reflection from the mirror, and rotation of the mirror about its rotation axis will thus control the elevation of the reflection, it being understood, however, that azimuth and elevation are used here only as relative orthogonal directions described, only for convenience, in the orientation of the preferred embodiment in which the longitudinal axis of the member is vertical. Similarly, it will be appreciated that exclusively orthogonal reflection control depends upon orienting the mirror rotation axis normal to the axis of the member, whereas operation of the invention merely requires that the mirror rotation axis have some component normal to the axis of the member, that is, generally normal thereto.

The preferred embodiment uses the mirror to reflect a beam of light to various locations on a screen of a visual field tester. In this embodiment the member is a tube which encloses the strand and mirror so as not to distract the patient's fixation on a fixation target even though the member and mirror are just in front of the patient's eye so as to project the light beam to all portions of the screen without blocking the patient's view. The strand mirror moving arrangement also allows the tube to be slim, again to minimally distract or block the patient's view. The strand mirror movement is also silent, again to avoid distracting the patient, and motors for moving the winch and member can be placed on the support to be more remote from the patient for quiet and for rapid operation by not having to move the mass of the motors.

DESCRIPTION OF THE DRAWINGS

The above and other features of the preferred embodiment which is intended to illustrate, but not to limit the invention will now be described with reference to drawings of the preferred embodiment in which.

DESCRIPTION OF THE PREFERRED EMBODIMENT

Figure 1:
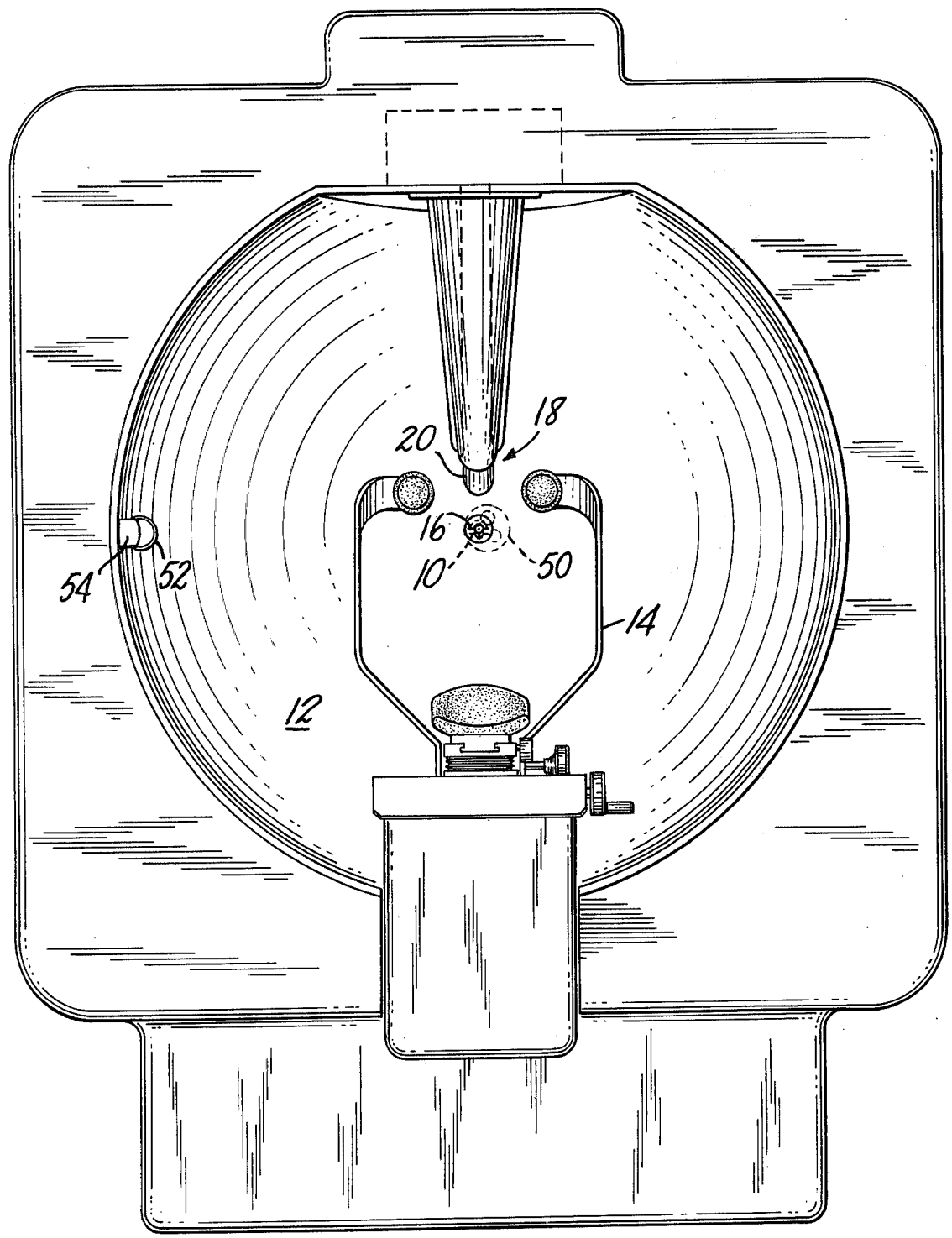
FIG. 1 is a front view of the preferred embodiment.

The preferred embodiment shown in FIG. 1 is a visual field tester in which a beam of light from a source 10 is projected to various locations on an hemispheric screen 12. A patient's eye to be tested is positioned by locating the patient's head in a rest 14 and the axis of the patient's vision fixed by directing the patient to look at a fixation target 16 in the center of the screen. The patient's ability to see the spot of light from the light beam in various locations on the screen is then an indication of the visual field of the patient's eye.

The spot of light is projected onto various locations on the screen with a precisely movable mirror mount at 18. The mirror mount is immediately in front of the patient and ends just above the eye being examined so as to be able to project the light spot to all portions of the screen and not block the patient's view. This location between the patient and the sound-reflecting hemispheric screen makes it important that the mount be small and silent in operation so as to avoid distracting the patient from fixating on the fixation target by sight or sound, including cuing the patient as to the direction of the testing light spot. As a further aid to this, the entire mount is encased in a fixed, tubular housing 20.

Figure 2:
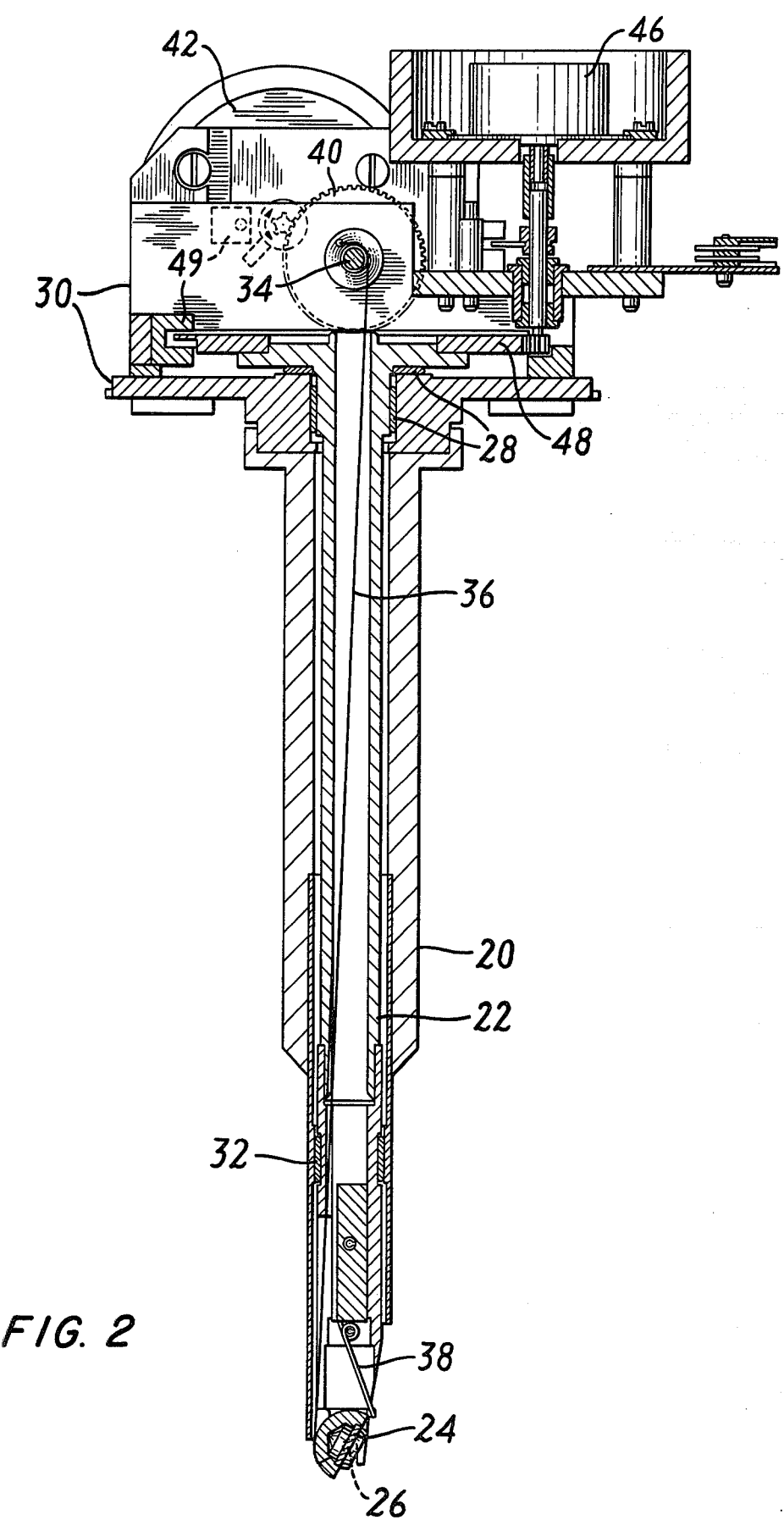
FIG. 2 is an elevation, partly in section, of a portion of the embodiment shown in FIG. 1.

As shown in FIG. 2, the mirror mount has an inner, tubular, elongated member 22. The member 22 supports a mirror 24 on a pivot pin 26 at a U-shaped end of the member where the tubular housing 20 is also cut away on the side generally remote from the patient to expose the mirror for reflecting the light beam to the screen. For convenience in predicting the reflection of the mirror, the rotational axis of the pivot pin 26 is on the reflective surface of the mirror, and intersects and is normal to the longitudinal axis of the member 22.

The other end of the member 22 spaced from the mirror is supported for rotation about the longitudinal axis of the member by bearings 28 on a support 30 which also supports the outer, stationary tube 20 at the margin of the screen. The member 22 is also guided for rotation in the outer tube by additional bearings 32.

The support 30 also supports a winch 34 over the member. One end of a strand 36 which preferably is a wire rope selected to be stretch and thermal expansion resistant is windingly connected to the winch. The strand then runs from the winch through the tubular member 22 to the mirror to which it is connected at its other end at a margin of the mirror spaced from the rotation axis of the mirror. Winding the strand on the winch thus rotates the mirror in one direction. A spring 38 connected between the member 22 and the mirror urges the mirror for rotation in the other direction to keep the strand under sufficient tension to prevent play and to rotate the mirror when the strand is unwound from the winch.

The winch is connected to a gear segment 40 which is rotated by a stepping motor 42 also on the support 30. The spring 38 also serves to prevent backlash in the winch drive. Another stepping motor 46 on the support 30 rotationally drives the margin of an enlarged end portion 48 of the member 22 to rotate the member about its longitudinal axis. The winch and the motors for rotating the winch and member are thus all fixedly supported on the support so that their mass does not have to be moved. This allows faster, more accurate movement of the mirror, the resulting slight twisting of the strand as the member rotates having a negligible effect on the mirror position. Photosensors 49 associated with each motor identify a known position of each motor from which the member of steps to another position identifies the position of the motors and thus the mirror position.

Returning to FIG. 1, the light source 10 includes a rotatable disc 50 having various sized apertures to control the size of the beam and thus the light spot on the screen by selecting the aperture through which the beam passes. Also associated with the light source is a pair of photosensors 52, 54, one for sensing the ambient light level reflected from the screen and one for sensing the intensity of the light spot when reflected to the sensor from the mirror. Comparison of the two light levels sensed by the photosensors and suitable rheostats or preferably filters (not shown) for controlling the source 10 and ambient lighting then further allow determination of the patient's visual field at different relative light intensities.

The operation of the preferred embodiment can now be described. With the patient's eye located by the rest 14 and its visual axis directed at the fixation target, the light spot of selected size and relative intensity reflected from the source by the mirror to the screen is moved to various positions. The stepping motor control, which preferably is a digital computer (not shown), records the number of steps of each motor from the photosensors 49 and thus the position of the light spot on the screen, the rotation of the member 22 by its motor 46 controlling the azimuth of the spot, and rotation of the mirror by its motor 42 controlling the spot elevation. The light spot can thus be moved along meridians on the screen until the patient reports, for example, that it cannot be seen. The respective motor steps can then be identified (preferably recorded in the computer) to identify a series of points which, when connected (again preferably with the computer), plot an isopter of the patient's vision under the preset conditions of spot size and intensity. The stepping motors and computer thus make possible an automated visual field tester, while the strand and member mirror control make the mirror mount small and its movement silent by spacing the motors away from the patient so as not to distract the patient. The response of the system is additionally made rapid because the motors themselves do not have to be moved.

We claim:

1. A precisely movable mirror mount device, comprising:
    an elongated member;
    a mirror pivotally supported on the member for rotation about an axis generally normal to the longitudinal axis of the member;
    support means spaced along the member from the mirror for supporting the member for rotation about the longitudinal axis of the member;
    a winch on the support means;
    a strand windingly connected at one end to the winch and connected at the other end to the mirror at a distance from the rotation axis of the mirror for rotating the mirror in one direction; and
    bias means connected between the mirror and the member for urging rotation of the mirror in the other direction.

2. In a device for testing a patient's visual field having means for positioning one of the patient's eyes for testing, a screen for viewing with the patient's positioned eye, fixation means for allowing the patient to fix the direction of vision toward the screen, and means including a light beam source for projecting a light spot onto various locations on the screen the perception of which with the patient's positioned eye of fixated direction indicates the visual field of that eye, an improved target projector device comprising:

- an elongated member having an end adjacent the patient's positioned eye and extending therefrom outside the patient's view of the screen;
- a mirror pivotally supported on the end of the member for rotation about an axis generally normal to the longitudinal axis of the member and in a position for reflecting the light beam from the source to the screen, whereby to provide the light spot on the screen;
- support means spaced along the member from its end to a position outside the patient's view of the screen for supporting the member for rotation about the longitudinal axis of the member, whereby to vary the azimuth of the light spot on the screen;
- a winch on the support means;
- a strand windingly connected at one end to the winch and connected at the other end to the mirror at a distance from the rotation axis of the mirror for rotating the mirror in one direction, whereby to vary the elevation of the light spot on the screen; and
- bias means connected between the mirror and the member for urging rotation of the mirror in the other direction.

3. A device as in claim 1 or 2, and further comprising means on the support for rotating the member and the winch.

4. A device in claim 3, wherein the means for rotating the member comprises a stepping motor.

5. A device as in claim 3, wherein the means for rotating the winch comprise a gear segment connected to the winch, a stepping motor for rotating the gear segment, and means for preventing backlash between the gear and motor.

6. A device as in claim 1 or 2, wherein the strand is a wire rope.

7. A device as in claim 1 or 2, wherein the bias means is a spring.

8. A device as in claim 1 or 2, and further comprising a stationary housing about the member.

9. A device as in claim 2, and further comprising means for controlling the diameter of the light beam from the source.

10. A device as in claim 2, and further comprising means for sensing the relative intensity of the light spot on the screen.

* * * * *